United States Patent
Kimberley et al.

(10) Patent No.: US 7,148,304 B2
(45) Date of Patent: Dec. 12, 2006

(54) POLYMERIZATION CATALYSTS

(75) Inventors: Brian Stephen Kimberley, Surrey (GB); Peter James Maddox, Middlesex (GB); Stephen Roy Partington, Surrey (GB)

(73) Assignee: BP Chemicals Limited, London (GB)

( * ) Notice: Subject to any disclaimer, the term of this patent is extended or adjusted under 35 U.S.C. 154(b) by 318 days.

(21) Appl. No.: 10/667,859

(22) Filed: Sep. 23, 2003

(65) Prior Publication Data

US 2004/0077489 A1  Apr. 22, 2004

Related U.S. Application Data

(60) Division of application No. 09/659,589, filed on Sep. 11, 2000, now Pat. No. 6,657,026, which is a continuation of application No. PCT/GB99/00714, filed on Mar. 10, 1999.

(30) Foreign Application Priority Data

| Mar. 12, 1998 | (GB) | ................... | 9805336.6 |
| Mar. 20, 1998 | (GB) | ................... | 9806106.2 |
| Mar. 27, 1998 | (GB) | ................... | 9806661.6 |
| May 7, 1998 | (GB) | ................... | 9809598.7 |
| Jul. 3, 1998 | (GB) | ................... | 9814496.7 |
| Sep. 16, 1998 | (GB) | ................... | 9820036.3 |
| Nov. 2, 1998 | (GB) | ................... | 9823983.3 |

(51) Int. Cl.
C08F 210/02 (2006.01)

(52) U.S. Cl. .................... 526/348; 526/352; 526/161

(58) Field of Classification Search ................ 526/348, 526/352, 161
See application file for complete search history.

(56) References Cited

U.S. PATENT DOCUMENTS 5,955,555 A * 9/1999 Bennett ................... 526/133

6,262,196 B1  7/2001 Meckling

FOREIGN PATENT DOCUMENTS

| JP | 10-007712 | * | 1/1998 |
| WO | WO 97/48735 | | 12/1997 |
| WO | WO 98/38228 | | 9/1998 |
| WO | WO 98/44011 | | 10/1998 |

* cited by examiner

Primary Examiner—Ling-Sui Choi
(74) Attorney, Agent, or Firm—Finnegan, Henderson, Farabow, Garrett and Dunner, L.L.P.

(57) ABSTRACT

A catalyst for the polymerization of 1-olefins is disclosed, which comprises (1) a compound of Formula B wherein M is Fe[II], Fe[III], Co[I], Co[II], Co[III], Mn[I], Mn[II], Mn[III], Mn[IV], Ru[II], Ru[III] or Ru[IV]; X represents an atom or group covalently or ionically bonded to the transition metal M; T is the oxidation state of the transition metal M and b is the valency of the atom or group X; $R^1$, $R^2$, $R^3$, $R^4$, $R^5$, $R^6$ and $R^7$ are independently selected from hydrogen, halogen, hydrocarbyl, substituted hydrocarbyl, heterohydrocarbyl or substituted heterohydrocarbyl; and when any two or more of $R^1$–$R^7$ are hydrocarbyl, substituted hydrocarbyl, heterohydrocarbyl or substituted heterohydrocarbyl, said two or more can be linked to form one or more cyclic substituents; and (2) a further catalyst. Copolymers made using the catalyst having specific physical properties are also disclosed

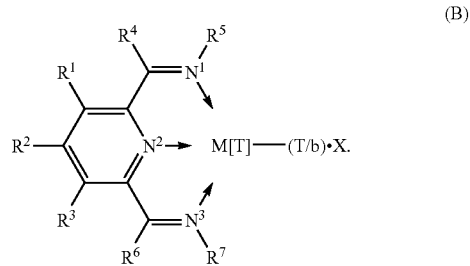

7 Claims, 2 Drawing Sheets

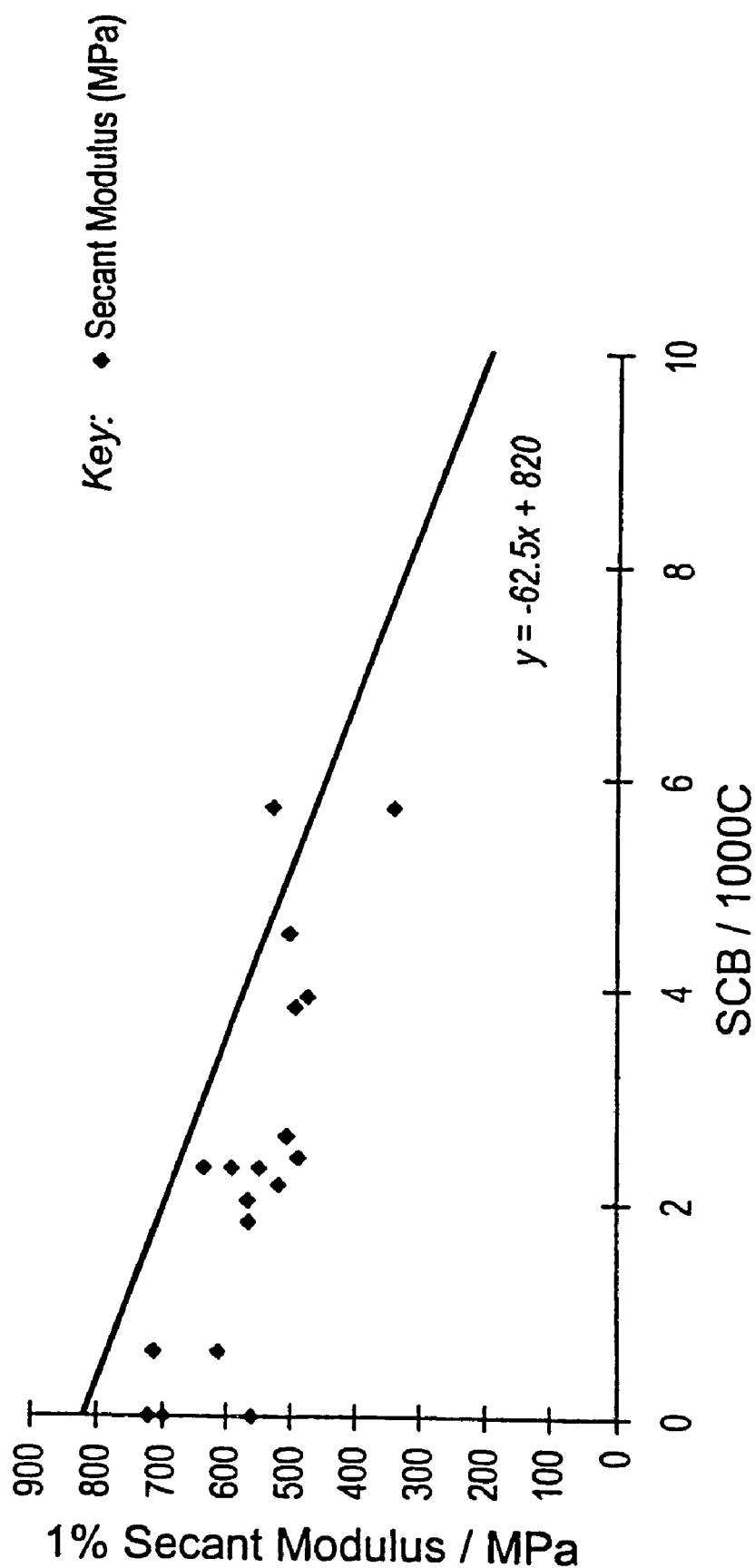

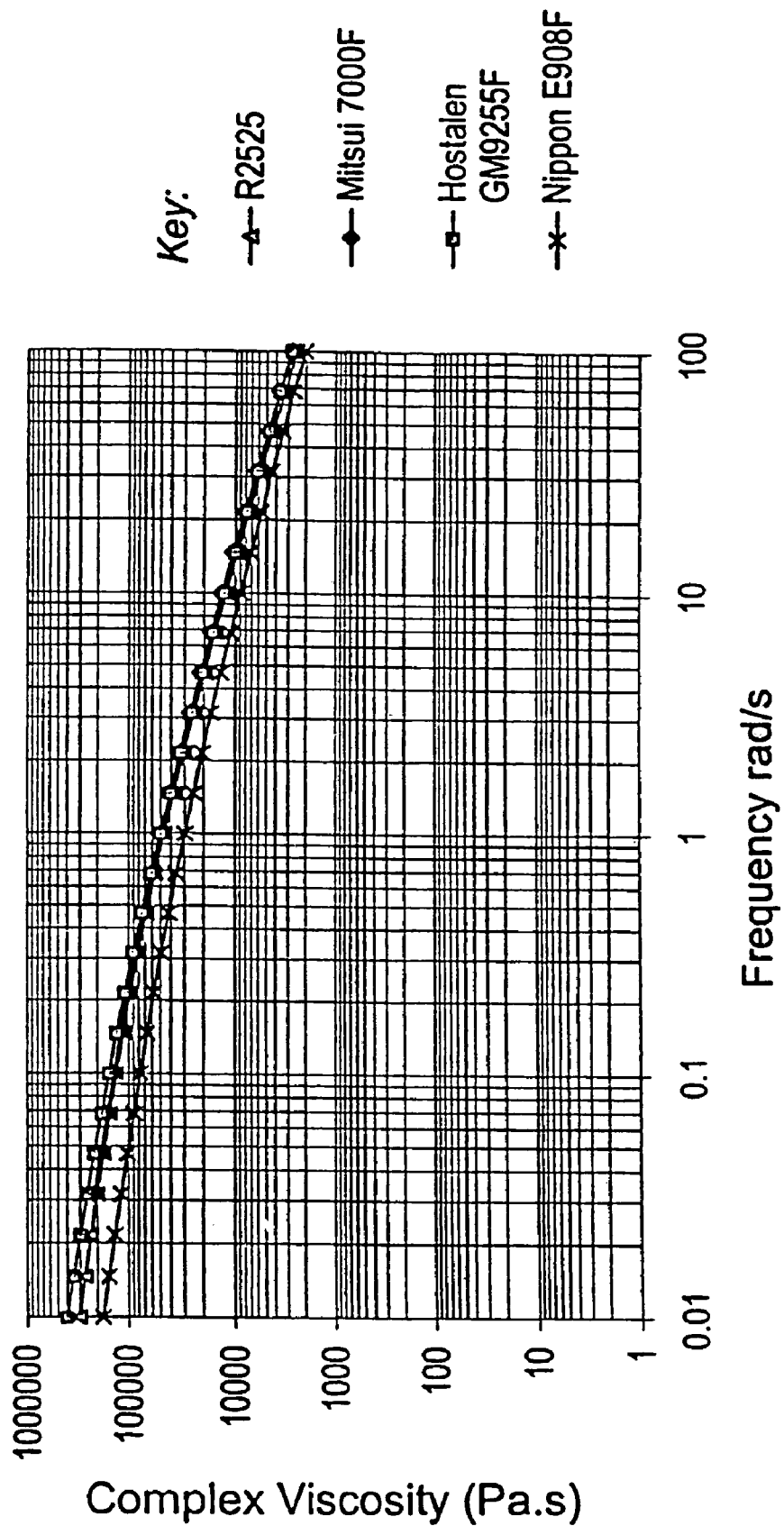

POLYMERIZATION CATALYSTS

This application is a divisional of application Ser. No. 09/659,589, filed Sep. 11, 2000, now U.S. Pat. No. 6,657,026, which is a continuation of International application PCT/GB 99/00714, filed Mar. 10, 1999, both of which are incorporated herein by reference.

BACKGROUND OF THE INVENTION

The present invention relates to novel transition metal compounds and to their use as polymerisation catalysts.

The use of certain transition metal compounds to polymerise 1-olefins, for example, ethylene, is well established in the prior art. The use of Ziegler-Natta catalysts, for example, those catalysts produced by activating titanium halides with organometallic compounds such as triethylaluminium, is fundamental to many commercial processes for manufacturing polyolefins. Over the last twenty or thirty years, advances in the technology have led to the development of Ziegler-Natta catalysts which have such high activities that that olefin polymers and copolymers containing very low concentrations of residual catalyst can be produced directly in commercial polymerisation processes. The quantities of residual catalyst remaining in the produced polymer are so small as to render unnecessary their separation and removal for most commercial applications. Such processes can be operated by polymerising the monomers in the gas phase, or in solution or in suspension in a liquid hydrocarbon diluent. Polymerisation of the monomers can be carried out in the gas phase (the "gas phase process"), for example by fluidising under polymerisation conditions a bed comprising the target polyolefin powder and particles of the desired catalyst using a fluidising gas stream comprising the gaseous monomer. In the so-called "solution process" the (co)polymerisation is conducted by introducing the monomer into a solution or suspension of the catalyst in a liquid hydrocarbon diluent under conditions of temperature and pressure such that the produced polyolefin forms as a solution in the hydrocarbon diluent. In the "slurry process" the temperature, pressure and choice of diluent are such that the produced polymer forms as a suspension in the liquid hydrocarbon diluent. These processes are generally operated at relatively low pressures (for example 10–50 bar) and low temperature (for example 50 to 150° C.).

Commodity polyethylenes are commercially produced in a variety of different types and grades. Homopolymerisation of ethylene with transition metal based catalysts leads to the production of so-called "high density" grades of polyethylene. These polymers have relatively high stiffness and are useful for making articles where inherent rigidity is required. Copolymerisation of ethylene with higher 1-olefins (e.g. butene, hexene or octene) is employed commercially to provide a wide variety of copolymers differing in density and in other important physical properties. Particularly important copolymers made by copolymerising ethylene with higher 1-olefins using transition metal based catalysts are the copolymers having a density in the range of 0.91 to 0.93. These copolymers which are generally referred to in the art as "linear low density polyethylene" are in many respects similar to the so called "low density" polyethylene produced by the high pressure free radical catalysed polymerisation of ethylene. Such polymers and copolymers are used extensively in the manufacture of flexible blown film.

An important feature of the microstructure of the copolymers of ethylene and higher 1-olefins is the manner in which polymerised comonomer units are distributed along the "backbone" chain of polymerised ethylene units. The conventional Ziegler-Natta catalysts have tended to produce copolymers wherein the polymerised comonomer units are clumped together along the chain. To achieve especially desirable film properties from such copolymers the comonomer units in each copolymer molecule are preferably not clumped together, but are well spaced along the length of each linear polyethylene chain. In recent years the use of certain metallocene catalysts (for example biscyclopentadienylzirconiumdichloride activated with alumoxane) has provided catalysts with potentially high activity and capable of providing an improved distribution of the comonomer units. However, metallocene catalysts of this type suffer from a number of disadvantages, for example, high sensitivity to impurities when used with commercially available monomers, diluents and process gas streams, the need to use large quantities of expensive alumoxanes to achieve high activity, and difficulties in putting the catalyst on to a suitable support.

WO98/27124, published after the earliest priority date of this invention, discloses that ethylene may be polymerised by contacting it with certain iron or cobalt complexes of selected 2,6-pyridinecarboxaldehydebis(imines) and 2,6-diacylpyridinebisimines); and our own copending application GB 9718775.1 has disclosed polymerisation catalysts containing novel nitrogen-containing transition metal compounds which comprise the skeletal unit depicted in Formula B:

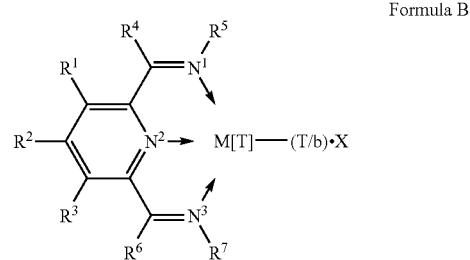

Formula B wherein M is Fe[II], Fe[III], Co[I], Co[II], Co[III], Mn[I], Mn[II], Mn[III], Mn[IV], Ru[II], Ru[III] or Ru[IV]; X represents an atom or group covalently or ionically bonded to the transition metal M; T is the oxidation state of the transition metal M and b is the valency of the atom or group X; $R^1$, $R^2$, $R^3$, $R^4$, $R^5$, $R^6$ and $R^7$ are independently selected from hydrogen, halogen, hydrocarbyl, substituted hydrocarbyl, heterohydrocarbyl or substituted heterohydrocarbyl; and when any two or more of $R^1$–$R^7$ are hydrocarbyl, substituted hydrocarbyl, heterohydrocarbyl or substituted heterohydrocarbyl, said two or more can be linked to form one or more cyclic substituents.

An object of the present invention is to provide a novel catalyst system suitable for polymerising monomers, for example, olefins, and especially for polymerising ethylene alone or for copolymerising ethylene with higher 1-olefins. A further object of the invention is to provide an improved process for the polymerisation of olefins, especially of ethylene alone or the copolymerisation of ethylene with higher 1-olefins to provide homopolymers and copolymers having controllable molecular weights.

SUMMARY OF THE INVENTION

We have unexpectedly discovered that the combination of catalysts of the Formula B with other catalysts can produce a highly active catalytic system in which the resultant polymers exhibit improved performance and processing properties.

The present invention provides a polymerisation catalyst comprising (1) a compound of the Formula B:

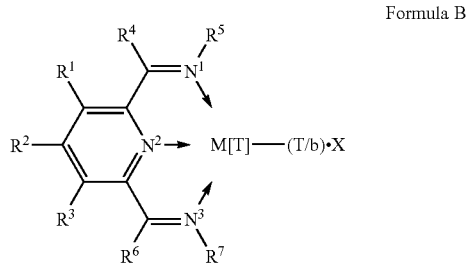

Formula B wherein M is Fe[II], Fe[III], Co[I], Co[II], Co[III], Mn[I], Mn[II], Mn[III], Mn[IV], Ru[II], Ru[III] or Ru[IV]; X represents an atom or group covalently or ionically bonded to the transition metal M; T is the oxidation state of the transition metal M and b is the valency of the atom or group X; $R^1$, $R^2$, $R^3$, $R^4$, $R^5$, $R^6$ and $R^7$ are independently selected from hydrogen, halogen, hydrocarbyl, substituted hydrocarbyl, heterohydrocarbyl or substituted heterohydrocarbyl; and when any two or more of $R^1$–$R^7$ are hydrocarbyl, substituted hydrocarbyl, heterohydrocarbyl or substituted heterohydrocarbyl, said two or more can be linked to form one or more cyclic substituents; and (2) a further catalyst.

BRIEF DESCRIPTION OF THE DRAWINGS

In the drawings:

FIG. 1 is a plot of secant modules (MPa) versus comonomer content trend; and

FIG. 2 is a plot of complex viscosity versus frequency (rad/s).

DETAILED DESCRIPTION OF THE INVENTION

The catalysts (1) and (2) can if desired both be a transition metal compound of Formula B. The catalyst may comprise, for example, a mixture of 2,6-diacetylpyridinebis(2,6-diisopropylanil)FeCl$_2$ complex and 2,6-diacetylpyridinebis(2,4,6-trimethylanil)FeCl$_2$ complex, or a mixture of 2,6-diacetylpyridine(2,6-disopropylanil)CoCl$_2$ and 2,6-diacetylpyridinebis(2,4,6-trimethylanil)FeCl$_2$. However preferably the further catalyst (2) is not covered by the definition of (1).

The further catalyst (2) may be for example, a Ziegler Natta catalyst, a Phillips type (chromium oxide) catalyst or a metallocene catalyst. Other catalysts (2) include monocyclopentadienyl constrained geometry type catalysts and bidentate α-diimine late transition metal catalysts. Metallocenes may typically be represented by the general formula:

where
($C_5R_x$)$_n$ and ($C_5R_m$) are cyclopentadienyl ligands,
R is hydrogen, alkyl, aryl, alkenyl, etc.
M is a Group IVA metal
Z is a bridging group,
L is an anionic ligand, and
y is 0, 1 or 2, n and m are 1–5, x is 0 or 1.

The most preferred complexes are those wherein y is 1 and L is halide or alkyl. Typical examples of such complexes are bis(cyclopentadienyl)zirconium dichloride and bis(cyclopentadienyl zirconium dimethyl. In such metallocene complexes the cyclopentadienyl ligands may suitably be substituted by alkyl groups such as methyl, n-butyl or vinyl. Alternatively the R groups may be joined together to form a ring substituent, for example indenyl or fluorenyl. The cyclopentadienyl ligands may be the same or different. Typical examples of such complexes are bis(n-butylcyclopentadienyl) zirconium dichloride or bis (methylcyclopentadienyl)zirconium dichloride.

Examples of monocyclopentadienyl- or constrained geometry complexes may be found in EP 416815A, EP 420436A, EP 418044A and EP 491842A the disclosures of which are incorporated herein by reference. A typical example of such a moncyclopentadienyl complex is (tert-butylamido)(tetramethyl cyclopentadienyl) dimethyl silanetitanium dimethyl.

Further examples of metallocene complexes are those wherein the anionic ligand represented in the above formula is replaced with a diene moiety. In such complexes the transition metal may be in the +2 or +4 oxidation state and a typical example of this type of complex is ethylene bis indenyl zirconium (II) 1,4-diphenyl butadiene. Examples of such complexes may be found in EP 775148A the disclosure of which is incorporated herein by reference.

Monocyclopentadienyl complexes having diene moieties have also been used for the polymerisation of olefins. Such complexes may be exemplified by (tert-butylamido)(tetramethylcyclopentadienyl) dimethylsilanetitanium (II) penta-1,3-diene. Such complexes are described in EP 705269A the disclosure of which is incorporated herein by reference.

Other transition metal complexes which may comprise catalyst (2) above are complexes having hetero ring ligands attached to the transition metal, for example O, NR or S ligands. Such complexes are disclosed for example in EP 735057A and may be illustrated by indenyl zirconium tris(diethylcarbamate).

The further catalyst (2) preferably comprises a heterogeneous catalyst or a supported catalyst which provides a support for the catalyst (1). It is preferred that the catalyst additionally incorporates (3) an activating quantity of an activator compound comprising a Lewis acid capable of activating the catalyst for olefin polymerisation, preferably an organoaluminium compound or a hydrocarbylboron compound.

The activator compound for the catalysts of the present invention is suitably selected from organoaluminium compounds and hydrocarbylboron compounds. Suitable organoaluminium compounds include trialkyaluminium compounds, for example, trimethylaluminium, triethylaluminium, tributylaluminium, tri-n-octylaluminium, ethylaluminium dichloride, diethylaluminium chloride and alumoxanes. Alumoxanes are well known in the art as typically the oligomeric compounds which can be prepared by the controlled addition of water to an alkylaluminium compound, for example trimethylaluminum. Such compounds can be linear, cyclic or mixtures thereof. Commercially available alumoxanes are generally believed to be mixtures of linear and cyclic compounds. The cyclic alumoxanes can be represented by the formula $[R^{16}AlO]_s$ and the linear alumoxanes by the formula $R^{17}(R^{18}AlO)_s$, wherein s is a number from about 2 to 50, and wherein $R^{16}$, $R^{17}$, and $R^{18}$ represent hydrocarbyl groups, preferably $C_1$ to $C_6$ alkyl groups, for example methyl, ethyl or butyl groups.

Examples of suitable hydrocarbylboron compounds are dimethylphenylammoniumtetra(phenyl)borate, trityltetra(phenyl)borate, triphenylboron, dimethylphenylammonium tetra(pentafluorophenyl)borate, sodium tetrakis[(bis-3,5-trifluoromethyl)phenyl]borate, $H^+(OEt_2)$[(bis-3,5-trifluoromethyl)phenyl]borate, trityltetra(pentafluorophenyl)borate and tris(pentafluorophenyl)boron.

In the preparation of the catalysts of the present invention the quantity of activating compound selected from organoaluminium compounds and hydrocarbylboron compounds to be employed is easily determined by simple testing, for example, by the preparation of small test samples which can be used to polymerise small quantities of the monomer(s) and thus to determine the activity of the produced catalyst. It is generally found that the quantity employed is sufficient to provide 0.1 to 20,000 atoms, preferably 1 to 2000 atoms of aluminium or boron per Fe, Co, Mn or Ru metal atom in the compound of Formula A In a preferred embodiment, the catalyst (1) is supported on a heterogeneous catalyst as catalyst (2), for example, a magnesium halide supported Ziegler Natta catalyst, a Phillips type (chromium oxide) supported catalyst or a supported metallocene catalyst. Formation of the supported catalyst can be achieved for example by treating the transition metal compounds of the present invention with alumoxane in a suitable inert diluent, for example a volatile hydrocarbon, slurrying a particulate support material with the product and evaporating the volatile diluent. The quantity of support material employed can vary widely, for example from 100,000 to 1 grams per gram of metal present in the transition metal compound. A particularly preferred support is a Ziegler Natta catalyst.

In a further aspect of the present invention compound (1) comprises the skeletal unit depicted in Formula Z:

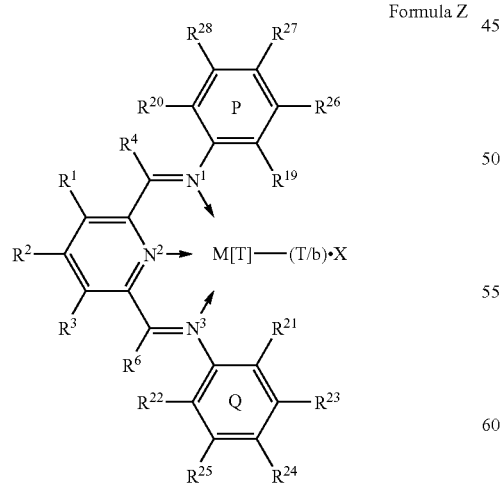

wherein M is Fe[II], Fe[III], Co[I], Co[II], Co[III], Mn[I], Mn[II], Mn[III], Mn[IV], Ru[II], Ru[III] or Ru[IV]; X represents an atom or group covalently or ionically bonded to the transition metal M; T is the oxidation state of the transition metal M and b is the valency of the atom or group X; $R^1$ to $R^4$, $R^6$ and $R^{19}$ to $R^{28}$ are independently selected from hydrogen, halogen, hydrocarbyl, substituted hydrocarbyl, heterohydrocarbyl or substituted heterohydrocarbyl; when any two or more of $R^1$ to $R^4$, $R^6$ and $R^{19}$ to $R^{28}$ are hydrocarbyl, substituted hydrocarbyl, heterohydrocarbyl or substituted heterohydrocarbyl, said two or more can be linked to form one or more cyclic substituents; with the proviso that at least one of $R^{19}$, $R^{20}$, $R^{21}$ and $R^{22}$ is hydrocarbyl, substituted hydrocarbyl, heterohydrocarbyl or substituted heterohydrocarbyl when neither of the ring systems P and Q forms part of a polyaromatic fused-ring system. In this particular aspect of the present invention, in the case that neither of the ring systems P and Q forms part of a polyaromatic ring system, it is preferred that at least one of $R^{19}$ and $R^{20}$, and at least one of $R^{21}$ and $R^{22}$ is selected from hydrocarbyl, substituted hydrocarbyl, heterohydrocarbyl or substituted heterohydrocarbyl, and most preferably each of $R^{19}$, $R^{20}$, $R^{21}$ and $R^{22}$ is selected from hydrocarbyl, substituted hydrocarbyl, heterohydrocarbyl or substituted heterohydrocarbyl.

In a further aspect of the present invention compound (1) comprises the skeletal unit depicted in Formula Z:

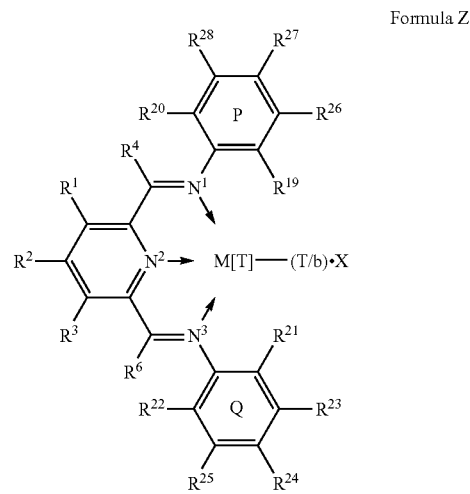

wherein M is Fe[II], Fe[III], Co[I], Co[II], Co[III], Mn[I], Mn[II], Mn[III], Mn[IV], Ru[II], Ru[III] or Ru[IV]; X represents an atom or group covalently or ionically bonded to the transition metal M; T is the oxidation state of the transition metal M and b is the valency of the atom or group X; $R^1$ to $R^4$, $R^6$ and $R^{19}$ to $R^{20}$ are independently selected from hydrogen, halogen, hydrocarbyl, substituted hydrocarbyl, heterohydrocarbyl or substituted heterohydrocarbyl; when any two or more of $R^1$ to $R^4$, $R^6$ and $R^{19}$ to $R^{28}$ are hydrocarbyl, substituted hydrocarbyl, heterohydrocarbyl or substituted heterohydrocarbyl, said two or more can be linked to form one or more cyclic substituents; with the proviso that $R^{19}$, $R^{20}$, $R^{21}$ and $R^{22}$ are hydrocarbyl, substituted hydrocarbyl, heterohydrocarbyl or substituted heterohydrocarbyl when neither of the ring systems P and Q forms part of a polyaromatic fused-ring system.

Subject to the foregoing provisos regarding $R^{19}$, $R^{20}$, $R^{21}$ and $R^{22}$ in Formula Z, $R^1$ to $R^4$, $R^6$ and $R^{19}$ to $R^{28'}$ in the compounds depicted in Formulae B and Z of the present invention are preferably independently selected from hydrogen and $C_1$ to $C_8$ hydrocarbyl, for example, methyl, ethyl, n-propyl, n-butyl, n-hexyl, and n-octyl. In Formula B, $R^5$ and $R^7$ are preferably independently selected from substituted or unsubstituted alicyclic, heterocyclic or aromatic groups, for example, phenyl, 1-naphthyl, 2-naphthyl, 2-methylphenyl, 2-ethylphenyl, 2,6-diisopropylphenyl, 2,3-diisopropylphenyl, 2,4-diisopropylphenyl, 2,6-di-n-butylphenyl, 2,6-dimethylphenyl, 2,3-dimethylphenyl, 2,4-dimethylphenyl, 2-t-butylphenyl, 2,6-diphenylphenyl, 2,4,6-trimethylphenyl, 2,6-trifluoromethylphenyl, 4-bromo-2,6-dimethylphenyl, 3,5 dichloro2,6-diethylphenyl, and 2,6,bis(2,6-dimethylphenyl)phenyl, cyclohexyl and pyridinyl.

The ring systems P and Q in Formula Z are preferably independently 2,6-hydrocarbylphenyl or fused-ring polyaromatic, for example, 1-naphthyl, 2-naphthyl, 1-phenanthrenyl and 8-quinolinyl.

In yet a further aspect of the present invention, compound (1) comprises the skeletal unit depicted in Formula T:

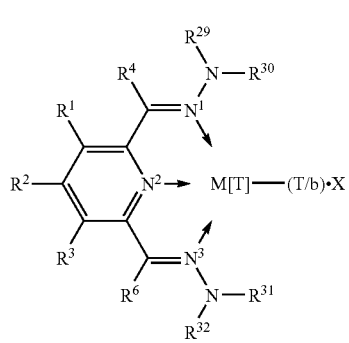

Formula T wherein M is Fe[II], Fe[III], Co[I], Co[II], Co[III], Mn[I], Mn[II], Mn[III], Mn[IV], Ru[II], Ru[III] or Ru[IV]; X represents an atom or group covalently or ionically bonded to the transition metal M; T is the oxidation state of the transition metal M and b is the valency of the atom or group X; $R^1$ to $R^4$, $R^6$ and $R^{29}$ to $R^{32}$ are independently selected from hydrogen, halogen, hydrocarbyl, substituted hydrocarbyl, heterohydrocarbyl or substituted heterohydrocarbyl; when any two or more of $R^1$ to $R^4$, $R^6$ and $R^{29}$ to $R^{32}$ are hydrocarbyl, substituted hydrocarbyl, heterohydrocarbyl or substituted heterohydrocarbyl, said two or more can be linked to form one or more cyclic substituents In the compound of Formula B of the present invention, M is preferably Fe[II]. In the compounds of Formula Z or Formula T of the present invention, M is preferably Fe[II], Mn[II] or Co[III].

Examples of the atom or group X in the compounds of Formula B, Z and T are halide, for example, chloride, bromide; iodide; hydride; hydrocarbyloxide, for example, methoxide, ethoxide, isopropoxide, phenoxide; carboxylate, for example, formate, acetate, benzoate; hydrocarbyl, for example, methyl, ethyl, propyl, butyl, octyl, decyl, phenyl, benzyl; substituted hydrocarbyl; heterohydrocarbyl; tosylate; and triflate. Preferably X is selected from halide, hydride and hydrocarbyl. Chloride is particularly preferred.

A particularly preferred embodiment of the present invention comprises a polymerisation catalyst comprising (1) as the transition metal compound, the Formula B or Formula Z or Formula T compound, (2) a further catalyst (preferably not covered by the definition of (1)), and preferably also (3) an activating quantity of an activator compound comprising a Lewis acid capable of activating the catalyst for olefin polymerisation, preferably an organoaluminium compound or a hydrocarbylboron compound. When catalyst (2) is a Ziegler-Natta catalyst, then it is preferred that components (1) and (3) are premixed prior to addition to (2).

In a further aspect of the present invention the polymerisation catalyst system additionally comprises (4) a neutral Lewis base.

In this further aspect of the present invention, the transition metal compound is preferably of Formula B, Z or T. The iron and cobalt compounds are preferred. The preferences in relation to the activator compound are the same as expressed above in relation to the catalysts of the present invention. Neutral Lewis bases are well known in the art of Ziegler-Natta catalyst polymerisation technology. Examples of classes of neutral Lewis bases suitably employed in the present invention are unsaturated hydrocarbons, for example, alkenes or alkynes, primary, secondary and tertiary amines, amides, phosphoramides, phosphines, phosphites, ethers, thioethers, nitriles, carbonyl compounds, for example, esters, ketones, aldehydes, carbon monoxide and carbon dioxide, sulphoxides, sulphones and boroxines. Although 1-olefins are capable of acting as neutral Lewis bases, for the purposes of the present invention they are regarded as monomer or comonomer 1-olefins and not as neutral Lewis bases per se. However, alkenes which are internal olefins, for example, 2-butene and cyclohexene are regarded as neutral Lewis bases in the present invention. Preferred Lewis bases are tertiary amines and aromatic esters, for example, dimethylaniline, diethylaniline, tributylamine, ethylbenzoate and benzylbenzoate. In this particular aspect of the present invention, components (1), (2), (3) and (4) of the catalyst system can be brought together simultaneously or in any desired order. However, if components (3) and (4) are compounds which interact together strongly, for example, form a stable compound together, it is preferred to bring together either components (1), (2) and (3) or components (1), (2) and (4) in an initial step before introducing the final defined component. Preferably components (1), (2) and (4) are contacted together before component (3) is introduced. The quantities of components (1), (2) and (3) employed in the preparation of this catalyst system are suitably as described above in relation to the catalysts of the present invention. The quantity of the neutral Lewis Base (component (4)) is preferably such as to provide a ratio of component (1)+(2): component (4) in the range 100:1 to 1:1000, most preferably in the range 1:1 to 1:20. Components (1), (2) and (4) of the catalyst system can be brought together, for example, as the neat materials, as a suspension or solution of the materials in a suitable diluent or solvent (for example a liquid hydrocarbon), or, if at least one of the components is volatile, by utilising the vapour of that component. The components can be brought together at any desired temperature. Mixing the components together at room temperature is generally satisfactory. Heating to higher temperatures e.g. up to 120° C. can be carried out if desired, e.g. to achieve better mixing of the components. It is preferred to carry out the bringing together of components (1), (2) and (4) in an inert atmosphere (eg dry nitrogen) or in vacuo. If it is desired to use the catalyst on a support material (see below), this can be achieved, for example, by preforming the catalyst system comprising components (1), (2), (3) and (4) and impregnating the support material preferably with a solution thereof, or by introducing to the support material one or more of the components simultaneously or sequentially. If desired the support material itself can have the properties of a neutral Lewis base and can be employed as, or in place of, component (4). An example of a support material having neutral Lewis base properties is poly(aminostyrene) or a copolymer of styrene and aminostyrene (ie vinylaniline). In an alternative preferred embodiment, components (2) and (3) are mixed together prior to the addition of component (1). This is particularly preferred when catalyst (2) is itself the support, such that catalyst (1) and the activator (3) are added separately to the support. In a further alternative catalyst (2) and activator (3) are added separately to catalyst (1).

The following are examples of nitrogen-containing transition metal complexes (1):
2,6-diacetylpyridinebis(2,6-diisopropylanil)FeCl$_2$
2,6-diacetylpyridine(2,6-disopropylanil)MnCl$_2$
2,6-diacetylpyridine(2,6-diisopropylanil)CoCl$_2$
2,6-diacetylpyridinebis(2-tert.-butylanil)FeCl$_2$
2,6-diacetylpyridinebis(2,3-dimethylanil)FeCl$_2$
2,6-diacetylpyridinebis(2-methylanil)FeCl$_2$
2,6-diacetylpyridinebis(2,4-dimethylanil)FeCl$_2$
2,6-diacetylpyridinebis(2,6-dimethylanil)FeCl$_2$
2,6-diacetylpyridinebis(2,6-dimethylanil)FeCl$_2$
2,6-dialdiminepyridinebis(2,4,6-trimethylanil)FeCl$_2$
2,6-dialdiminepyridinebis(2,6-diethylanil)FeCl$_2$
2,6-dialdiminepyridinebis(2,6-diisopropylanil)FeCl$_2$
2,6-dialdiminepyridinebis(1-naphthil)FeCl$_2$ and
2,6-bis(1,1-diphenylhydrazone)pyridine.FeCl$_2$.

The present invention further provides a process for the polymerisation or copolymerisation of 1-olefins, comprising contacting the monomeric olefin(s) under polymerisation conditions with a polymerisation catalyst comprising (1) a compound based on the Formula B, T or Z, and (2) a further catalyst. The further catalyst (2) is preferably not covered by the above definition (1). In a preferred process the catalyst additionally comprises an activating quantity of an activator compound comprising a Lewis acid capable of activating the catalyst for olefin polymerisation, preferably an organoaluminium compound or a hydrocarbylboron compound. The process of the invention may also comprise the additional step of blowing the resultant polymer into a film.

The catalysts (1) and (2) may be contacted with the olefin to be polymerised in the form of a single catalyst system, or they may be added to the reactor separately.

The process/catalyst of the invention is especially useful for copolymerising ethylene with other 1-olefins One disadvantage of the catalysts disclosed in GB 9718775.1 A, where the only catalyst in the system is catalyst (1) as defined in this invention, is that they produce copolymers having only a relatively low level of comonomer incorporation for a given level of comonomer in the reaction vessel. We have discovered that the catalyst system of the present invention can produce copolymers having significantly higher levels of comonomer incorporation for the same level of comonomer reactant. Thus in a preferred process for the copolymerisation of ethylene and a further 1-olefin, particularly a 1-olefin having 6 or more carbon atoms, the degree of short chain branching per thousand carbons (SCB) in the resultant copolymer is greater than zero and also equal to or greater than 18.18R−0.16 where R is the ratio of partial pressure of further 1-olefin to that of ethylene. Preferably the SCB is greater than or equal to 18.18R−0.05, more preferably 18.18R−0.04. A further aspect of the invention provides a copolymer of ethylene and a further 1-olefin having an SCB of 2.0, preferably 3.0 or greater and comprising residues of a nitrogen-containing iron complex, wherein the iron concentration is from 0.01 to 1000 parts by weight per million parts of copolymer, preferably 0.01 to 10 ppm by weight, for example 0.11 to 1.03 ppm by weight.

The process of the invention also permits the short chain branching to be preferentially located in a particular portion of the molecular weight distribution of the copolymer. Thus a further aspect of the invention provides a method of selecting the portion of the molecular weight distribution of a copolymer of ethylene and a further 1-olefin in which units of said further 1-olefin are located, comprising contacting the monomeric olefins under polymerisation conditions with a polymerisation catalyst comprising (1) a compound based on the Formula B, T or Z, and (2) a further catalyst not covered by the above definition (1). Preferably the 1-olefin has 6 or more carbon atoms. In a preferred method the portion of the molecular weight distribution of the copolymer in which units of the further 1-olefin are located is within the 50% by weight of the copolymer having the highest molecular weight. A further aspect of the invention provides a copolymer of ethylene and a further 1-olefin, particularly a 1-olefin having 6 or more carbon atoms, comprising residues of a nitrogen-containing iron complex wherein the iron concentration is from 0.01 to 10 parts by weight per million parts of copolymer, and in which at least 50%, preferably at least 60% and more preferably at least 70% of the short chain branching is located within the 50% by weight of the copolymer having the highest molecular weight. Generally it is preferred that at least 80% of the short chain branching is located within the 80% by weight of the copolymer having the highest molecular weight.

Copolymerisation permits the control of physical properties of the polymer such as density and environmental stress crack resistance; however it generally results in polymers having reduced modulus (rigidity). High modulus (or rigidity) is necessary for pipe and moulding products where the ability to support hydrostatic loads is important, and in film applications where is reduces the degree of sag and misalignment which can occur during film production or handling. The use of the catalyst system of the present invention where the heterogeneous catalyst is a Ziegler-Natta catalyst is capable of producing copolymers having a higher modulus for a given comonomer content than has hitherto been possible, and a better blend of physical properties such as those mentioned above.

Accordingly in a further aspect the present invention provides a copolymer of ethylene and a further 1-olefin wherein the degree of short chain branching per thousand carbons (SCB) is from 2.0 to 10, and the relationship of modulus in MPa (M) to SCB (B) is defined by the equation M=k−62.5B where k is 820 or greater.

Whilst many copolymers are known having SCB greater than 2, the particular combination of high SCB, which, for example, is desirable in tough films, and high modulus has not hitherto been achievable. The preferred range of SCB is between 2 and 8, though more preferably SCB is greater than 2.5, and most preferably greater than 3.0. The relationship between modulus and SCB is preferably such that k is 830 or greater, more preferably 840 or greater, and particularly 850 or greater. A preferred relationship is defined by the equation M=k−65.5B where k is 850 or greater, a more preferred one by the equation M=k−67.5B where k is 870 or greater, and a particularly preferred one by the equation M=k−70.5B where k is 90or greater. Another preferred relationship is defined by the equation M=k−60B where k is 815 or greater, a more preferred one by the equation M=k−57.5B where k is 810 or greater, and a particularly preferred one by the equation M=k−55B where k is 805 or greater. In FIG. 1 a plot of modulus against SCB is shown, which demonstrates the region attainable by the invention but not by known copolymers. Points are shown on the graph not only for copolymers according to the invention, but also for known copolymers. The region covered by the invention is that on or above the diagonal line, and between SCB/1000C=2.0 and 10.

Preferred comonomers are olefins having from 4 to 8 carbons, such as 1-butene, 1-hexene, 4-methylpentene-1, and octene.

The above copolymers are generally preferred to have high molecular weights for maximum impact performance. However the high viscosity of such materials can create problems during processing, for example with film blowing, such as high stresses and energy consumption during compounding and processing, degradation of the polymer, unbalanced machine direction and transverse direction tear strengths, and poor downgauging performance. This can make it difficult or impossible to produce tough thin (10–15 micron) film. It is therefore necessary to ensure that products suitable for film applications have a molecular weight distribution which lowers high shear (extrusion) viscosity while maintaining other desirable features. The copolymers of this aspect of the invention have rheology comparable to other commercially available processable tough film grades (FIG. 2). The viscosity-shear rate dependence shown graphically in FIG. 2 can be modelled by the Carreau equation which extrapolates the curve to calculate the zero shear rate viscosity. Thus the copolymer of Example 32.5 has a rheology defined by the equation $\eta=(4.455\times10^6)[1+1.776\chi^{0.1286}]^{(-0.070/0.1286)}$ where $\eta$ is viscosity at 180° C. and $\chi$ is the shear rate. The zero shear viscosity of the copolymer of Example 32.5 is therefore intermediate between that of the other two commercial grades. Copolymers of this aspect of the invention are preferred to have a zero shear viscosity of between $0.1\times10^6$ Ps and $12\times10^6$ Ps.

The polymers and copolymers of the invention are generally made in the form of a powder, the particle size of which may be from 0.1 to 18 mm diameter. Pellets may also be made, having a diameter of 0.2 to 30 mm.

The polymerisation conditions employed in the process of the invention can be, for example, solution phase, slurry phase or gas phase. If desired, the catalyst can be used to polymerise the olefin under high pressure/high temperature process conditions wherein the polymeric material forms as a melt in supercritical ethylene. Preferably the polymerisation is conducted under gas phase fluidised bed conditions. Suitable monomers for use in the polymerisation process of the present invention are, for example, ethylene, propylene, butene, hexene, methyl methacrylate, methyl acrylate, butyl acrylate, acrylonitrile, vinyl acetate, and styrene. Preferred monomers for homopolymerisation processes are ethylene and propylene.

Slurry phase polymerisation conditions or gas phase polymerisation conditions are particularly useful for the production of high density grades of polyethylene. In these processes the polymerisation conditions can be batch, continuous or semi-continuous. In the slurry phase process and the gas phase process, the catalyst is generally fed to the polymerisation zone in the form of a particulate solid. In the case of catalyst (1) (and also catalyst (2) if this too is a compound according to formula B), this solid may be an undiluted solid catalyst system formed from a nitrogen-containing complex and an activator, or can be the solid complex alone. In the latter situation, the activator can be fed to the polymerisation zone, for example as a solution, separately from or together with the solid complex. Preferably the catalyst system or the transition metal complex component of the catalyst system employed in the slurry polymerisation and gas phase polymeriastion is supported on a support material. Most preferably the catalyst system is supported on a support material prior to its introduction into the polymerisation zone. Suitable support materials are, for example, silica, alumina, zirconia, talc, kieselguhr, or magnesia. Impregnation of the support material can be carried out by conventional techniques, for example, by forming a solution or suspension of the catalyst components in a suitable diluent or solvent, and slurrying the support material therewith. The support material thus impregnated with catalyst can then be separated from the diluent for example, by filtration or evaporation techniques.

In the slurry phase polymerisation process the solid particles of catalyst, or supported catalyst, are fed to a polymerisation zone either as dry powder or as a slurry in the polymerisation diluent. Preferably the particles are fed to a polymerisation zone as a suspension in the polymerisation diluent. The polymerisation zone can be, for example, an autoclave or similar reaction vessel, or a continuous loop reactor, eg of the type well-know in the manufacture of polyethylene by the Phillips Process. When the polymerisation process of the present invention is carried out under slurry conditions the polymerisation is preferably carried out at a temperature above 0° C., most preferably above 15° C. The polymerisation temperature is preferably maintained below the temperature at which the polymer commences to soften or sinter in the presence of the polymerisation diluent. If the temperature is allowed to go above the latter temperature, fouling of the reactor can occur. Adjustment of the polymerisation within these defined temperature ranges can provide a useful means of controlling the average molecular weight of the produced polymer. A further useful means of controlling the molecular weight is to conduct the polymerisation in the presence of hydrogen gas which acts as chain transfer agent. Generally, the higher the concentration of hydrogen employed, the lower the average molecular weight of the produced polymer.

The use of hydrogen gas as a means of controlling the average molecular weight of the polymer or copolymer applies generally to the polymerisation process of the present invention. For example, hydrogen can be used to reduce the average molecular weight of polymers or copolymers prepared using gas phase, slurry phase or solution phase polymerisation conditions. The quantity of hydrogen gas to be employed to give the desired average molecular weight can be determined by simple "trial and error" polymerisation tests.

The polymerisation process of the present invention provides polymers and copolymers, especially ethylene polymers, at remarkably high productivity (based on the amount of polymer or copolymer produced per unit weight of nitrogen containing transition metal complex employed in the catalyst system). This means that relatively very small quantities of catalyst are consumed in commercial processes using the process of the present invention. It also means that when the polymerisation process of the present invention is operated under polymer recovery conditions that do not employ a catalyst separation step, thus leaving the catalyst, or residues thereof, in the polymer (eg as occurs in most commercial slurry and gas phase polymerisation processes), the amount catalyst in the produced polymer can be very small. Experiments carried out with the catalyst of the present invention show that, for example, polymerisation of ethylene under slurry polymerisation conditions can provide a particulate polyethylene product containing catalyst so diluted by the produced polyethylene that the concentration of transition metal therein falls to, for example, 1 ppm or less wherein "ppm" is defined as parts by weight of transition metal per million parts by weight of polymer. Thus polyethylene produced within a polymerisation reactor by the process of the present invention may contain catalyst diluted with the polyethylene to such an extent that the transition metal content thereof is, for example, in the range of 1–0.0001 ppm, preferably 1–0.001 ppm. Using a catalyst comprising a nitrogen-containing Fe complex in accordance with the present invention in, for example, a slurry polymerisation, it is possible to obtain polyethylene powder wherein the Fe concentration is, for example, 1.03 to 0.11 parts by weight of Fe per million parts by weight of polyethylene.

Methods for operating gas phase polymerisation processes are well known in the art. Such methods generally involve agitating (e.g. by stirring, vibrating or fluidising) a bed of catalyst, or a bed of the target polymer (i.e. polymer having the same or similar physical properties to that which it is desired to make in the polymerisation process) containing a catalyst, and feeding thereto a stream of monomer at least partially in the gaseous phase, under conditions such that at least part of the monomer polymerises in contact with the catalyst in the bed. The bed is generally cooled by the addition of cool gas (eg recycled gaseous monomer) and/or volatile liquid (eg a volatile inert hydrocarbon, or gaseous monomer which has been condensed to form a liquid). The polymer produced in, and isolated from, gas phase processes forms directly a solid in the polymerisation zone and is free from, or substantially free from liquid. As is well known to those skilled in the art, if any liquid is allowed to enter the polymerisation zone of a gas phase polymerisation process the quantity of liquid is small in relation to the quantity of polymer present in the polymerisation zone. This is in contrast to "solution phase" processes wherein the polymer is formed dissolved in a solvent, and "slurry phase" processes wherein the polymer forms as a suspension in a liquid diluent.

The gas phase process can be operated under batch, semi-batch, or so-called "continuous" conditions. It is preferred to operate under conditions such that monomer is continuously recycled to an agitated polymerisation zone containing polymerisation catalyst, make-up monomer being provided to replace polymerised monomer, and continuously or intermittently withdrawing produced polymer from the polymerisation zone at a rate comparable to the rate of formation of the polymer, fresh catalyst being added to the polymerisation zone to replace the catalyst withdrawn form the polymerisation zone with the produced polymer.

In the preferred embodiment of the gas phase polymerisation process of the present invention, the gas phase polymerisation conditions are preferably gas phase fluidised bed polymerisation conditions.

Methods for operating gas phase fluidised bed processes for making polyethylene and ethylene copolymers are well known in the art. The process can be operated, for example, in a vertical cylindrical reactor equipped with a perforated distribution plate to support the bed and to distribute the incoming fluidising gas stream through the bed. The fluidising gas circulating through the bed serves to remove the heat of polymerisation from the bed and to supply monomer for polymerisation in the bed. Thus the fluidising gas generally comprises the monomer(s) normally together with some inert gas (e.g. nitrogen) and optionally with hydrogen as molecular weight modifier. The hot fluidising gas emerging from the top of the bed is led optionally through a velocity reduction zone (this can be a cylindrical portion of the reactor having a wider diameter) and, if desired, a cyclone and or filters to disentrain fine solid particles from the gas stream. The hot gas is then led to a heat exchanger to remove at least part of the heat of polymerisation. Catalyst is preferably fed continuously or at regular intervals to the bed. At start up of the process, the bed comprises fluidisable polymer which is preferably similar to the target polymer. Polymer is produced continuously within the bed by the polymerisation of the monomer(s). Preferably means are provided to discharge polymer from the bed continuously or at regular intervals to maintain the fluidised bed at the desired height. The process is generally operated at relatively low pressure, for example, at 10 to 50 bars, and at temperatures for example, between 50 and 120° C. The temperature of the bed is maintained below the sintering temperature of the fluidised polymer to avoid problems of agglomeration.

In the gas phase fluidised bed process for polymerisation of olefins the heat evolved by the exothermic polymerisation reaction is normally removed from the polymerisation zone (ie, the fluidised bed) by means of the fluidising gas stream as described above. The hot reactor gas emerging from the top of the bed is led through one or more heat exchangers wherein the gas is cooled. The cooled reactor gas, together with any make-up gas, is then recycled to the base of the bed. In the gas phase fluidised bed polymerisation process of the present invention it is desirable to provide additional cooling of the bed (and thereby improve the space time yield of the process) by feeding a volatile liquid to the bed under conditions such that the liquid evaporates in the bed thereby absorbing additional heat of polymerisation from the bed by the "latent heat of evaporation" effect. When the hot recycle gas from the bed enters the heat exchanger, the volatile liquid can condense out. In one embodiment of the present invention the volatile liquid is separated from the recycle gas and reintroduced separately into the bed. Thus, for example, the volatile liquid can be separated and sprayed into the bed. In another embodiment of the present invention the volatile liquid is recycled to the bed with the recycle gas. Thus the volatile liquid can be condensed from the fluidising gas stream emerging from the reactor and can be recycled to the bed with recycle gas, or can be separated from the recycle gas and sprayed back into the bed.

The method of condensing liquid in the recycle gas stream and returning the mixture of gas and entrained liquid to the bed is described in EP-A-0089691 and EP-A-0241947. It is preferred to reintroduce the condensed liquid into the bed separate from the recycle gas using the process described in our U.S. Pat. No. 5,541,270, the teaching of which is hereby incorporated into this specification.

When using the catalysts of the present invention under gas phase polymerisation conditions, the catalyst, or one or more of the components employed to form the catalyst can, for example, be introduced into the polymerisation reaction zone in liquid form, for example, as a solution in an inert liquid diluent. Thus, for example, the transition metal component, or the activator component, or both of these components can be dissolved or slurried in a liquid diluent and fed to the polymerisation zone. Under these circumstances it is preferred the liquid containing the component(s) is sprayed as fine droplets into the polymerisation zone. The droplet diameter is preferably within the range 1 to 1000 microns. EP-A-0593083, the teaching of which is hereby incorporated into this specification, discloses a process for introducing a polymerisation catalyst into a gas phase polymerisation. The methods disclosed in EP-A-0593083 can be suitably employed in the polymerisation process of the present invention if desired.

The present invention is illustrated in the following Examples.

EXAMPLES

Example 9

9.1 Preparation of 2.6-diacetylpyridinebis(2.4.6-trimethylanil)

To a solution of 2,6-diacetylpyridine (0.54 g; 3.31 mmol) in absolute ethanol (20 ml) was added 2,4,6-trimethylaniline (1.23 g; 2.5 eq.). After the addition of 2 drops of acetic acid (glacial) the solution was refluxed overnight. Upon cooling to room temperature the product crystallised from ethanol. The product was filtered, washed with cold ethanol and dried in a vacuum oven (50° C.) overnight. The yield was 60% of theoretical. $^1$H NMR(CDCl$_3$): 8.50, 7.95, 6.94, (m, 7H, ArH, pyrH), 2.33 (s, 6H, N=CCH$_3$), 2.28 (s, 6H, CCH$_3$), 2.05 (s, 12H, CCH$_3$). Mass spectrum: m/z 397 [M]$^+$.

9.2 Preparation of 2.6-diacetylpyridinebis(2.4.6-trimethylanil)FeCl$_2$

FeCl$_2$ (0.15 g; 1.18 mmol) was dissolved in hot n-butanol (20 ml) at 80° C. A suspension of 2,6-diacetylpyridinebis (2,4,6-trimethylaniline(0.5 g; 1.18 mmol) in n-butanol was added dropwise at 80° C. The reaction mixture turned blue. After stirring at 80° C. for 15 minutes the reaction was allowed to cool down to room temperature. The reaction volume was reduced to a few ml and diethyl ether was added to precipitate the product as a blue powder, which was subsequently washed three times with 10 ml diethyl ether. The yield was 64% of theoretical.

Mass spectrum: m/z 523 [M]$^+$, 488 [M–Cl]$^+$, 453 [M–Cl$_2$]$^+$.

Example 27 (Comparative)

This Example shows polymerisation using a catalyst system containing only a catalyst covered by the definition (1) in the present invention.

Preparation of the Supported Catalyst 2,6-diacetylpyridinebis(2,4,6-trimethylanil)FeCl$_2$ was prepared as described in Example 9. Silica (1.38 g ES70, supplied by Crosfield), which had been heated under flowing nitrogen at 700° C., was placed in a Schlenk tube and toluene (10 ml) was added.

To a solution of 2,6-diacetylpyridinebis(2,4,6-trimethylanil)FeCl$_2$ (0.041 g) in toluene (10 ml) was added methylaluminoxane (13.2 ml, 1.78M in toluene, supplied by Witco). This mixture was heated at 40° C. for 30 minutes to dissolve as much of the iron complex as possible. The solution was then transferred to the silica/toluene. The silica/MAO/toluene mixture was maintained at 40° C., with regular stirring, for 30 minutes before the toluene was removed, at 40° C., under vacuum to yield a free flowing powder. Analysis of the solid gave 16.9% w/w Al and 0.144% w/w Fe.

Polymerisation Tests

The reagents used in the polymerisation tests were: hydrogen Grade 6.0 (supplied by Air Products): ethylene Grade 3.5 (supplied by Air Products): hexene (supplied by Aldrich) distilled over sodium/nitrogen: dried pentane (supplied by Aldrich): methylaluminium (2M in hexanes, supplied by Aldrich): and triisobutylaluminium (1M in hexanes, supplied by Aldrich).

A 3 liter reactor was baked out under flowing nitrogen for at least 1 hour at 77–85° C. before powdered sodium chloride (300 g, predried under vacuum, 160° C., >4 hours) was added. The sodium chloride was used as a fluidisable/stirrable start-up charge powder for the gas phase polymerisation. Trimethyl aluminium (3 ml, 2M in hexanes) was added to the reactor and was boxed in nitrogen. The alkyl aluminium was allowed to scavenge for poisons in the reactor for between ½–1 hour before being vented using 4×4 bar nitrogen purges. The gas phase composition to be used for the polymerisation was introduced into the reactor and preheated to 77° C. prior to injection of the catalyst composition. The catalyst (0.18–0.22 g) was injected under nitrogen and the temperature then adjusted to 80° C. The ratio of hexene and/or hydrogen to ethylene during the polymerisation was kept constant by monitoring the gas phase composition by mass spectrometer and adjusting the balance as required. The polymerisation tests were allowed to continue for between 1 to 2 hours before being terminated by purging the reactants from the reactor with nitrogen and reducing the temperature to <30° C. The produced polymer was washed with water to remove the sodium chloride, then with acidified methanol (50 ml HCl/2.5 L methanol) and finally with water/ethanol (4:1 v/v). The polymer was dried under vacuum, at 40° C., for 16 hours. All the polymerisation tests were carried out at a polymerisation temperature of 80° C. and at an ethylene pressure of 8 bars. The polymerisation conditions are set out in the following Table.

TABLE 1

| Ex. | Other cocatalyst mmols | Temp ° C. | Ethylene barg | H$_2$ barg | hexene barg | SCB/ 1000 C |
|---|---|---|---|---|---|---|
| 27.3 | TMA$^\#$/6 | 80 | 8 | 0.5 | 0.2 | 0.1 |
| 27.7 | — | 80 | 8 | — | 0.86 | 1.6 |

$^\#$2M Solution of trimethylaluminium in toluene (supplied by Aldrich)

These results show the relatively low level of comonomer incorporation when only a single Fe based catalyst is used; the higher level in Example 27.7 required a much greater amount of hexene to be added.

Example 32

32.1—Preparation of a Supported Ziegler Catalyst Component

Silica (20 kg), grade ES 70 supplied by Crosfield, which had been dried at 800° C. for 5 hours in flowing nitrogen, was slurried in hexane (110 liters) and hexamethyldisilazane (30 moles), supplied by Fluka, was added with stirring at 50° C. Dry hexane (120 liters) was added with stirring, the solid allowed to settle, the supernatant liquid removed by decantation and further dry hexane (130 liters) was added with stirring. The hexane washing was repeated a further 3 times. Dibutylmagnesium (30 moles), supplied by FMC, was added and stirred for 1 hour at 50° C. Tertiary butyl chloride (60 moles) was added and stirred for 1 hour at 50° C. To this slurry was added an equimolar mixture of titanium tetrachloride (3 moles), and titanium tetra-n-propoxide (3 moles) with stirring at 50° C. for 2 hours, followed by 5 washings with dry hexane (130 liters). The slurry was dried under a flowing nitrogen stream to give a solid, silica supported Ziegler catalyst component.

32.2—Preparation of a Mixed Catalyst by Coimpregnation Containing a Ziegler Component and the Catalyst of Example 9

A solution of methylaluminoxane ("MAO", 10.2 mmol) as a 10% wt solution in toluene, supplied by Witco, was added to a suspension of 2,6-diacetylpyridinebis(2,4,6-trimethylanil)FeCl$_2$ (0.07 mmol in 5 ml dry toluene), prepared as in Example 9, and the mixture shaken for 5 minutes. This solution was then added to 2.0 g of the silica supported Ziegler catalyst prepared above (Example 32.1), the mixture shaken for 2 hours at 20° C. and then the solvent removed under reduced pressure at 20° C. to yield the mixed catalyst as a free flowing powder.

32.3–32.4—Preparation of Mixed Catalysts by Sequential Impregnation Containing a Ziegler Component and the Catalyst of Example 9

A sample of silica supported Ziegler catalyst (as prepared in 32.1 above) was placed in a schlenk tube and toluene (5 ml) added to form a slurry. Methylaluminoxane, MAO (1.78M in toluene, supplied by Witco) was added to the schlenk and the resultant slurry shaken intermittently at room temperature for 30 minutes. The supernatant liquid was removed and the solid washed with toluene (10 ml) at room temperature. The volatile components of the resultant solid were then removed under reduced pressure at 20° C. to yield a solid free flowing powder.

(2,6-diacetylpyridinebis(2,4,6 trimethyl anil) iron dichloride (prepared as described in Example 9 above) was added to a slurry of the above powder in toluene (10 ml) at room temperature for 1 hour. The mixture was occasionally shaken then the supernatant was removed by decantation and the resulting solid was dried under vacuum at 20° C.

Two catalysts were made by this method, with the amounts of each catalyst component ("Ziegler" and "Fe") and MAO used given below:

| Catalyst | Ziegler g | Fe mmol | MAO mmol | Ziegler/MAO washing (toluene) | Ziegler/MAO/Fe washing (hexane) |
|---|---|---|---|---|---|
| 32.3 | 2 | 0.070 | 10.45 | 1 × 10 ml | 2 × 5 ml |
| 32.4 | 2 | 0.073 | 3.56 | 1 × 10 ml | 2 × 5 ml |

32.5–32.18—Polymerisation of ethylene/hexene mixture using a mixed catalyst

A 3 liter reactor equipped with a helical stirrer was heated to 77–95° C. for 1 hour with dry nitrogen flowing through. Dry sodium chloride (300 g) was then added with trimethylaluminium (TMA) solution (2 ml of 2 molar TMA in hexane) and the reactor heated at 85° C. for 0.5–1 hours. The reactor was purged with nitrogen, cooled to 50° C. and TMA solution (3 ml of 2 molar TMA in hexane) added. The temperature was raised to 77° C. and hydrogen (0.5 bar) and ethylene (8 bar) added prior to the addition of 1-hexene (2.6 ml). Reaction was started by injection into the reactor of one of the mixed catalysts 32.2, 32.3 or 32.4 (0.1–0.3 g) prepared above. The temperature was maintained at 80° C. and ethylene added to maintain constant pressure. The gas phase was monitored by a mass spectrometer and hydrogen and 1-hexene added as necessary to maintain constant gas phase concentrations of these components. The polymerisation was carried out for 60 minutes. The polymer was washed with water to remove the sodium chloride, then with acidified methanol (50 ml HCVI/2.5 liters methanol) and finally with water/ethanol (4:1 v/v). The polymer was dried under vacuum, at 40° C. for 16 hours.

Details of the reactions are given in Table 2 below. For Examples 32.3 to 32.8, 32.10, 32.11 and 32.13, R=0.025 and 18.18R–0.16=0.29. For Example 32.9, R=0.050 and 18.18R–0.16=0.75. For Example 32.12, R=0.038 and 18.18R–0.16=0.51.

TABLE 2

| Ex. | Catalyst used | Catalyst Injected g | Gas phase co-catalyst/ mmols | Temp ° C. | Ethylene barg | H$_2$ barg | 1-hexene barg | Polymer Yield g | SCB/ 1000 C |
|---|---|---|---|---|---|---|---|---|---|
| 32.5 | 32.3 | 0.19 | TMA#/20 | 80 | 8 | 0.08 | 0.2 | 68 | 5.7 |
| 32.6 | 32.3 | 0.19 | TMA#/6 | 80 | 8 | 0.09 | 0.2 | 161 | 1.4 |
| 32.7 | 32.3 | 0.18 | TMA#/20 | 80 | 8 | 0.5 | 0.2 | 55 | 3.7 |
| 32.8 | 32.3 | 0.18 | TMA#/6 | 95 | 8 | 0.5 | 0.2 | 156 | 2.6 |
| 32.9 | 32.3 | 0.19 | TEA*/6 | 80 | 8 | 0.5 | 0.2 | 143 | 0.4 |
| 32.10 | 32.3 | 0.18 | TMA#/12 | 80 | 8 | 0.5 | 0.2 | 66 | 2.5 |
| 32.11 | 32.3 | 0.10 | TMA#/6 | 80 | 8 | 0.5 | 0.4 | 59 | 6.6 |
| 32.12 | 32.3 | 0.19 | TMA#/6 | 80 | 8 | 0.5 | 0.2 | 123 | 1.8 |
| 32.13 | 32.3 | 0.12 | TMA#/6 | 65 | 8 | 0.28 | 0.2 | 84 |  |
| 32.14 | 32.3 | 0.10 | TMA#/6 | 80 | 14 | 0.17 | 0.3 | 185 |  |
| 32.15 | 32.4 | 0.12 | TMA#/6 | 80 | 8 | 0.5 | 0.2 | 82 |  |
| 32.16 | 32.2 | 0.20 | TMA#/6 | 80 | 8 | 0.5 | 0.2 | 111 | 2.3 |
| 32.17 | 32.2 | 0.21 | TMA#/6 | 80 | 8 | 3 | 0.2 | 55 | 3.5 |
| 32.18 | 32.2 | 0.20 | TMA#/6 | 80 | 8 | 0.06 | 0.2 | 76 | 3.2 |

2M Solution of trimethylaluminium in toluene (supplied by Aldrich)
*1M Solution of triethylaluminium in hexanes (supplied by Aldrich)

The above table shows clearly that much higher levels of comonomer incorporation are achieved at relatively low levels of comonomer concentration by the used of the mixed catalyst system of the invention (compare Example 27.3, which also has a hexene partial pressure of 0.2 bar but an SCB of only 0.1/1000 C). The comonomer incorporation is also concentrated in the high molecular weight part of the copolymer.

Physical Properties of Product of Example 32.5

Modulus Measurement

Modulus test samples were compression moulded to a thickness of approximately 200 mm using a Moores hydraulic press. A picture frame mould was prepared by cutting a 25 cm square in a sheet of aluminium foil and sandwiching this frame between two sheets of melinex, aluminium sheet, and steel plates. 3 g of polymer was evenly arranged in the picture frame mould, which was then assembled and transferred to the press (pre-heated to 200° C.). The plattens were then closed to a contact pressure of 10 kg/cm² and held for 3 minutes after which full pressure (20 tons) was applied for 5 minutes. The press was then crash cooled with cold water running through the plattens with the pressure held at 20 tons. Once cool the pressure was released, mould disassembled, and the flash trimmed from the polymer sheet. For modulus measurement parallel sided specimens of dimensions 100 mm×5 mm were cut from each sheet and the exact dimensions accurately measured.

Samples were tested in an Instron using a 100N load cell at a strain rate of 2 mm/min. Samples were gripped with a pneumatic grip at the bottom and a manual screw grip at the the top so that the guage length (ungripped section) of the sample was 20 mm. The 1% secant modulus was calculated over the initial (1% strain) linear section of the stress-strain curve. Typically six specimens were tested and the results averaged.

The product of Example 32.5 was found to have a secant modulus of 529 MPa. It had an SCB of 5.7/1000 C. This values are plotted in FIG. 1 (the single point above the diagonal line), together with points corresponding to commercially available copolymers outside the scope of the invention.

The polymer of Example 32.5 had a broad molecular weight distribution (as determined by gel permeation chromatography. The polydispersity (Mw/Mn) was 28.5.

Dynamic Shear Rheometry Measurement 2 g of polymer sample (containing 0.2% Irganox 1010 antioxidant if uncompounded reactor powder used) was weighed out and distributed evenly around a steel mould shaped in form of disks 25 mm diameter and 2 mm in thickness. This mould was sandwiched between steel plates and placed in a press pre-heated to 190° C. The sample was exposed firstly to low pressure (10 kg/cm²) for 3 mins then high pressure (20 tons) for 5 mins, after which the press plattens were rapidly cooled via a supply of cold water. Once the plattens had reached room temperature the pressure was released and sample removed. Excess polymer flashing was removed prior to loading into the rheometer.

Sample rheology was measured with a Rheometrics RDS2 dynamic, strain-controlled rheometer at 180° C. using a strain of 5%, parallel plate geometry (25 mm diameter plates), over a frequency range of 0.01–100 rad/s.

A plot showing the complex viscosity of Example 32.3 compared with two commercial HDPE tough film grades is shown in FIG. 2; this demonstrates that the copolymer has acceptable Theological properties for commercial use.

Holtrop Analysis of the Polymer Produced in Example 32.5

Mixtures of 2-n-butoxyethanol, xylene and Irganox 1010 Ffat (0.15 g) were premeasured into round bottom flasks. Fraction 1 (see Table 3a below) was placed in a cruicible and heated to 120–122° C. A sample of polymer (5 g) was ground using a Reich mill (1 mm mesh) and added to the pre-heated solvent mixture. The polymer slurry was stirred 60 rpm for 20 minutes after which the liquid components of the mixture were drained through a microfilter, cooled and mixed with acetone (500 ml) in order to precipitate the dissolved polymer. The next solvent fraction was then added to the crucible and the procedure repeated in order for all the solvent ratios shown below. The isolated polymers were dried for 6 hours in a vacuum oven at 40° C. prior to analysis.

TABLE 3a

| FRACTION | Non-solvent 2-n-butoxyethanol (ml) | Solvent Xylene (ml) | TOTAL (ml) |
| --- | --- | --- | --- |
| 1 | 186 | 114 | 300 |
| 2 | 174 | 126 | 300 |
| 3 | 162 | 138 | 300 |
| 4 | 156 | 144 | 300 |
| 5 | 150 | 150 | 300 |
| 6 | 146 | 154 | 300 |
| 7 | 142 | 158 | 300 |
| 8 | 138 | 162 | 300 |
| 9 | 0 | 300 | 300 |
| | 1254 | 1446 | 2700 |

TABLE 3b

| Fraction | Mw (× 10³) | Mn (× 10³) | Mw/Mn | SCB/1000 C IR | SCB/1000 C ¹H NMR |
| --- | --- | --- | --- | --- | --- |
| Bulk | 304 | 20 | 15 | 6.5 | 5.8 |
| 1 | 8.3 | 2.21 | 3.76 | 1.3 | 3.8 |
| 2 | 21.3 | 6.16 | 3.46 | 5.9 | 4.9 |
| 3 | 41.5 | 13.2 | 3.14 | 6.3 | |
| 4 | 79.1 | 31.6 | 2.5 | 9 | 6.8 |
| 5 | 121.4 | 32.2 | 3.77 | 7.8 | |
| 6 | 109.2 | 38.9 | 2.81 | 7.2 | |
| 7 | 132.1 | 46.2 | 2.86 | 6.3 | |
| 8 | 318 | 36.4 | 4.8 | | |
| 9 | 582.3 | 127.6 | 4.56 | 3.3 | |

These results show that for a product derived from a multisite catalyst and being at the very earliest experimental stage (and therefore non-optimised), comonomer can be preferentially incorporated in a fraction of the copolymer with respect to product molecular weight.

Example 41

Example shows the use of a combination of a metallocene-type catalyst with a catalyst based on an iron complex of the present invention for polymerising ethylene under slurry conditions.

41.1—Preparation of a Supported Metallocene Catalyst

To silica (Crosfield grade ES70, previously calcined at 200° C. in flowing $N_2$ for 5 hrs) was added a toluene solution of methylaluminoxane (MAO) containing dissolved bis(n-butylcyclopentadienyl)ZrCl$_2$. The amounts used were 2.5 mmol MAO per gram of silica and 0.05 mmol metallocene per gram silica. The resulting slurry was stirred gently for at least 1 hour before being dried under reduced pressure to give a free flowing powder.

41.2—Preparation of the Combined Metallocene/Fe-complex Catalyst

The supported metallocene catalyst (2.5 g) prepared as described in step 41.1 above was placed in a Schlenk tube and a slurry of 2,6-diacetylpyridinebis(2,4,6 trimethyl anil) iron dichloride (73 mg) in hexane (10 ml) was added thereto at ambient temperature. The mixture was heated to 80° C. and left for 90 minutes with occasional shaking to maintain a well-mixed solution. There was no colouration evident in the supernatant solution above the solid. The produced catalyst was dried at 80° C. under vacuum to leave a dry free flowing powder.

41.3—Polymerisation of Ethylene

A 1 liter reactor was heated under flowing nitrogen for 1 hour at 80° C. before being cooled to 30° C. Triisobutyl aluminium (3 ml of 1M in hexanes) was added to the reactor followed by 500 ml of isobutane. The reactor was heated to 77° C. and the pressure increased to 12.9 bar. Ethylene was added to give 20.9 bar total pressure. The catalyst (0.100 g, slurried in hexane) prepared as described in 41.2 above was injected into the reactor. The ethylene pressure during the polymerisation was estimated to be approximately 8 bar. Polymerisation was allowed to continue for 60 minutes. 96 g of polymer was recovered. Analysis of the polymer by GPC indicated Mw and Mn to be 471000 and 30000 respectively.

Comparative Test 41.4

This shows the polymerisation of ethylene using only the supported metallocene catalyst described in step 41.1.

A 1 liter reactor was heated under flowing nitrogen for 1 hour at 80° C. before being cooled to 30° C. Triisobutyl aluminium (3 ml of 1M in hexanes) was added to the reactor followed by 500 ml of isobutane. The reactor was heated to 75° C. and the pressure increased to 12.7 bar. Ethylene was added to give 20.7 bar total pressure. The supported metallocene catalyst (0.094 g, slurried in hexane) prepared in step 41.1 above was injected into the reactor. The ethylene pressure during the polymerisation was estimated to be approximately 8 bar. Polymerisation was allowed to continue for 60 minutes. 49 g of polymer was recovered. Analysis of the polymer by GPC indicated Mw and Mn to be 142000 and 53000 respectively.

Example 42

This Example shows the use of a combination of a Phillips catalyst with a catalyst based on an iron complex of the present invention for polymerising ethylene under slurry conditions.

42.1 Preparation of Phillips Catalyst

To HA30WFL Phillips Cr on silica catalyst (Supplied by Grace, activated in flowing air for 5 hrs at 550° C., 295.1 g) was added a toluene solution of MAO (Witco, 515 ml×1.47 M, 0.76 mol). The addition took 30 minutes during which time the flask was gently swirled to ensure an even coating and the orange Cr catalyst turned chocolate brown. The slurry was placed in a waterbath at 50° C. for 1 hr and was shaken periodically to thoroughly mix. The solvent was then removed by vacuum at 50° C. until fluidisation of the catalyst had stopped, leaving a free flowing khaki-green powder. Yield=347.7 g. Analysis by ICP 5.96w/w % Al and 0.85w/w % Cr.

42.2 Preparation of mixed Phillips/2,6-diacetylpyridinebis(2.4.6-trimethylanil)FeCl$_2$ catalyst To the MAO treated Phillips catalyst of Example 42.1 (2.7 g) slurried in anhydrous hexane (10 ml) was added a slurry of 2,6-diacetylpyridinebis(2,4,6 trimethyl anil) iron dichloride from Example 9.2 (36 mg, 6.9×10$^{-2}$ mmol) in anhydrous hexane (10 ml). The resulting slurry was vigorously shaken for 10 mins, the solid allowed to settle and the colourless supernatant decanted. The remaining solid was washed with hot hexane (2×15 ml), decanted and pumped dry under vacuum at 50° C. until fluidisation of the solid had stopped yielding a green/brown free flowing powder. Iron loading calculated to be 0.14% w/w.

42.3—Polymerisation of Ethylene

A 1 L reactor was heated under flowing nitrogen for 1 hour at 90° C. before being cooled to 30° C. Triisobutyl aluminium (3 ml×1M in hexanes) followed by isobutane (500 ml) was added to the reactor. The reactor was sealed and heated to 80° C. raising the pressure to 13.9 bar. Ethylene was added to give 26.9 bar total pressure, the vessel was again sealed and cooled to 78° C. The catalyst of Example 42.2 (0.099 g, slurried in 5 cm$^3$ hexane) was injected into the reactor raising the pressure by 0.3 bar. The reactor pressure was controlled at 27.2 bar during the test (ethylene pressure estimated to be approximately 13.0 bar) and the temperature adjusted to 80° C. Polymerisation was allowed to continue for 120 minutes. 76.1 g of polymer was recovered. Analysis of the polymer by GPC indicated Mw and Mn to be 722000 and 15000 respectively (polydispersity=48.0).

Example 45

This Example shows the preparation of a further mixed catalyst comprising a Ziegler catalyst and the catalyst prepared in Example 9 above. The polymer made using this catalyst was blown into a film.

Pre-Impregnation of Support with Activator Compound

All the following operations were conducted under a nitrogen atmosphere unless stated. A sample of silica supported Ziegler catalyst was placed in a schlenk tube and toluene added to form a slurry. Methylaluminoxane, MAO (1.78M in toluene, supplied by Witco) was added to the schlenk tube and the resultant slurry mixed intermittently at room temperature. The supernatant liquid above the solid was removed and the solid washed with toluene at room temperature. The volatile components of the resultant material were then removed under reduced pressure at 20° C. to yield the solid as a free flowing powder. Four different supports were prepared, listed in Table 4 below.

TABLE 4

| Example | Silica supported Ziegler g | MAO mmol | MAO:Ti ratio | Toluene in slurry cm³ | Reaction time mins | Toluene wash cm³ |
|---|---|---|---|---|---|---|
| 45.1 | 20 | 104 | 25:1 | 50 | 30 | 100 |
| 45.2 | 50 | 261 | 25:1 | 125 | 30 | 125 |
| 45.3 | 80 | 418 | 25:1 | 100 | 60 | 100 |
| 45.4 | 80 | 167 | ... | 300 | 30 | 200 |

Supporting the Catalyst 2,6-diacetylpyridinebis(2,4,6 trimethyl anil) iron dichloride prepared as described in Example 9 above was added to a slurry of each of the four the solid supports in toluene at room temperature. The mixture was occasionally shaken, the supernatant solution removed, and the supported catalyst washed with toluene followed by a mixture of hexanes (hexane 40–60° C., supplied by Aldrich). The solid was dried under vacuum at 20° C. Table 5 below shows the preparative details for the four catalysts thus prepared.

TABLE 5

| Example | Support g | Fe mmol | MAO:Fe ratio | Toluene in slurry cm³ | Reaction time mins | Toluene wash cm³ | Hexane wash cm³ |
|---|---|---|---|---|---|---|---|
| 45.1 | 26 | 0.70 | 150:1 | 100 | 45 | 0 | 100 |
| 45.2 | 30 | 0.70 | 100:1** | 100 | 45 | 0 | 100 |
| 45.3 | 105 | 2.79 | 150:1 | 400 | 30 | 400 | 400 |
| 45.4 | 90 | 1.11 | 150:1 | 220 | 30 | 150 | 140 |

Preparation of Mixed Catalysts by Coimpregnation Containing a Ziegler Component and the Catalyst of Example 9

All the following operations were conducted under a nitrogen atmosphere unless stated. A solution of methylaluminoxane as a 10% wt solution in toluene, supplied by Witco, was added to a suspension of 2,6-diacetylpyridinebis(2,4,6-trimethylanil)FeCl$_2$, prepared as in Example 9, and the mixture shaken. This solution was then added to the silica supported Ziegler catalyst prepared above (Example 32.1) and the resultant slurry mixed intermittently at room temperature. The volatile components of the resultant material were then removed under reduced pressure at 20° C. to yield the mixed catalyst as a free flowing powder. The supported catalysts prepared, are listed below.

| Example | Silica Supported Ziegler g | MAO mmol | Fe mmol | MAO:Ti:Fe | Toluene in slurry cm³ | Reaction time mins |
|---|---|---|---|---|---|---|
| 45.5 | 200 | 348 | 8.40 | 41:5:1 | 400 | 30 |
| 45.6 | 100 | 139 | 1.68 | 83:12:1 | 200 | 30 |

Polymerisation

The six catalysts prepared above were used to polymerise ethylene. The polymerisation was conducted in a continuous fluidised bed reactor of 15 cm diameter.

Ethylene, n-hexene, hydrogen and TEA/TMA were fed into the reactor: starting with a seed-bed of polyethylene powder (approx. 1000 g), catalyst was injected into the reactor and the polymerisation carried out to increase the mass of the bed to approximately 3.5 kg. Polymerisation and product withdrawal was continued to yield a product substantially free of the starting bed. Process conditions for each of the polymerisations conducted are given in Table 6 below.

TABLE 6

| Example | Aluminium Alkyl | H$_2$ [bar] | Ethylene [bar] | Hexene [bar] | Al residue ppm | Ti residue ppm | Si residue ppm |
|---|---|---|---|---|---|---|---|
| 45.1 | TEA | 0.46 | 8 | 0.18 | 93 | 4.4 | 180 |
| 45.2a | TEA | 0.23 | 4 | 0.09 | 94 | 4.9 | 160 |
| 45.2b | TEA | 0.16 | 4 | 0.09 | 72 | 6 | 222 |
| 45.3 | TEA | 0.17 | 4 | 0.09 | 175 | 4.2 | 160 |
| 45.4 | TEA | 0.17 | 4 | 0.09 | 146 | 6.7 | 193 |
| 45.5a | TMA | 0.26 | 4 | 0.20 | 208 | 6.2 | 152 |
| 45.5b | TMA | 1.68 | 8 | 0.00 | 174 | 7.5 | 216 |
| 45.6 | TEA | 0.49 | 4 | 0.2 | 185 | 9.9 | 285 |

Properties of the polymers obtained for the above polymerisations are given in Table 7 below, with additional data for Examples 45.5a and 45.5b in Table 8.

TABLE 7

| Example | HLMI | Average HLMI | Density kg/m³ | Mn | Mw | Mw/Mn | Bu/1000 C |
|---|---|---|---|---|---|---|---|
| 45.1 | 3.5 | 3.5 | 945 | — | — | — | 1.6 |
| 45.2a | 5.2–4.2 | 4.5 | 952 | 15000 | 268000 | 18.4 | 0.7 |
| 45.2b | 3.3–3.8 | 4 | 951 | 19000 | 278000 | 14.4 | |

TABLE 7-continued

| Example | HLMI | Average HLMI | Density kg/m³ | Mn | Mw | Mw/Mn | Bu/1000 C |
|---|---|---|---|---|---|---|---|
| 45.3 | 2.98–3.7 | 3 | 951 | 19000 | 241000 | 12.4 | |
| 45.4 | 3.38–4 | 3.5 | 948 | 27000 | 245000 | 9.2 | |
| 45.5a | 10.5 | 10.5 | 951 | 23000 | 165000 | 7.1 | |
| 45.5b | 10.5 | 10.5 | 957 | 22000 | 234000 | 10.8 | |
| 45.6 | 11.5 | 11.5 | 950 | 26000 | 168000 | 6.4 | |

TABLE 8

| Example | PE Yield KgPE/gCatalyst | Average Particle Size (μm) | % Fines (<125 μm) | Span |
|---|---|---|---|---|
| 45.5a | 2.2 | 458 | 2.6 | 1.3 |
| 45.5b | 1.6 | 350 | 8.2 | 1.6 |

Compounding

The polymers in Table 6 were compounded: the powder extracted from the polymerisation reactor was stabilised with 1000 ppm of process antioxidant Irgafos PEPQ, 1000 ppm of a long term antioxidant Irganox 1010 and 1000 ppm of a neutralizer (calcium stearate). The blend of powder and additives was compounded in a twin screw extruder type Werner 53 equipped with two 53 mm diameter screws with a length/diameter ratio of 48. The temperature profile along the screw was between 220° C. and 240° C.

Film Blowing

The compounded polymers 45.1 to 45.4 were then extruded on an AXON BX18 type extruder with a die diameter of 70 mm, and a die gap of 1 mm. The screw diameter was 18 mm with a L/D ratio of 30. Details of the extrusion conditions are given in Table 9 below, together with the Film Appearance Rating (FAR), which is a measurement of the gels and fish-eyes content in each film sample.

TABLE 9

| | Example | | | | |
|---|---|---|---|---|---|
| | 45.1 | 45.2a | 45.2b | 45.3 | 45.4 |
| Temp profile (° C.) | 190–230 | 190–230 | 190–130 | 190–230 | 190–230 |
| Screw speed (revs/min) | 154 | 148 | 196 | 170 | 150 |
| Melt pressure (bar) | 428 | 468 | 495 | 497 | 488 |
| Melt temp (° C.) | 221 | 222 | 223 | 229 | 226 |
| Output (kg/hr) | 1.5 | 1.9 | 2.0 | 2.2 | 2.0 |
| Take off speed (m/min) | 2.1 | 2.5 | 3.0 | 2.5 | 2.5 |
| Blow Up Ratio | 2:1 | 2:1 | 2–3:1 | 2:1 | 2:1 |
| Frostline (mm) | min* | min | min | min | min |
| Motor load (Amps) | 3.10 | 3.06 | 3.0 | 2.97 | 3.19 |
| Film thickness (μm) | 12.32 | 22.30 | 18–26 | 25–32 | 22–26 |
| FAR | −40 | −40 | −20 | −30 | −20 |

*minimum frostline means that the change from molten to solid film occurred at the minimum distance from the air ring blowing the film.

The compounded polymers 45.5a, 45.5b and 45.6 were extruded on a Collin type extruder with a die diameter of 70 mm, and a die gap of 0.8 mm. Details of the extrusion conditions are given in Table 10 below, together with the Film Appearance Rating (FAR).

TABLE 10

| Example | 45.5a | 45.5b | 45.6 |
|---|---|---|---|
| Screw speed (revs/min) | 38 | 38 | 37 |
| Melt pressure (bar) | 460 | 430 | 417 |
| Melt temp (° C.) | 181 | 177 | 180 |
| Output (kg/hr) | 9 | 9 | 9 |
| Take off speed (m/min) | 14.4 | 14.4 | 14.2 |
| Blow Up Ratio | 3:1 | 3:1 | 3:1 |
| Motor load (Amps) | 16.9 | 15.5 | 15.6 |
| Film thickness (μm) | 17–22 | 16–20 | 14–22 |
| FAR | +20 | +20 | +20 |

These results show that for a product derived from a multisite catalyst and being at the very earliest experimental stage (and therefore non-optimised), the optical properties are surprisingly good. The relatively good film appearance rating FAR indicates that there are unexpectedly low gel levels in the film.

What is claimed is:

1. Copolymer of ethylene and a further 1-olefin wherein the degree of short chain branching per thousand carbons (SCB) is from 2.0 to 10, and the relationship of modulus in MPa (M) to SCB (B) is defined by the equation $M = k - 62.5B$ where k is 820 or greater.

2. Copolymer according to claim 1 wherein the SCB is between 2 and 8.

3. Copolymer according to claim 1 wherein the SCB is greater than 2.5.

4. Copolymer according to claim 1 wherein k is 830 or greater.

5. Copolymer according to claim 3 wherein SCB is greater than 3.0.

6. Copolymer according to claim 4 wherein k is 840 or greater.

7. Copolymer according to claim 6 wherein k is 850 or greater.

* * * * *